US009044471B2

(12) United States Patent
Green et al.

(10) Patent No.: US 9,044,471 B2
(45) Date of Patent: Jun. 2, 2015

(54) COMBINATIONS OF DOPAMINE D2 RECEPTOR BLOCKADE WITH NOREPINEPHRINE REUPTAKE INHIBITION AND WITH NOREPINEPHRINE ALPHA 2 RECEPTOR BLOCKADE

(76) Inventors: Alan I. Green, Hanover, NH (US); David Chau, White River Junction, VT (US)

( * ) Notice: Subject to any disclaimer, the term of this patent is extended or adjusted under 35 U.S.C. 154(b) by 0 days.

(21) Appl. No.: 12/024,950

(22) Filed: Feb. 1, 2008

(65) Prior Publication Data
US 2008/0188464 A1 Aug. 7, 2008

Related U.S. Application Data

(60) Provisional application No. 61/007,117, filed on Dec. 11, 2007, provisional application No. 60/887,657, filed on Feb. 1, 2007.

(51) Int. Cl.
| | | |
|---|---|---|
| *A61K 31/55* | (2006.01) | |
| *A61K 31/519* | (2006.01) | |
| *A61K 31/445* | (2006.01) | |
| *A61K 31/451* | (2006.01) | |
| *A61K 45/06* | (2006.01) | |

(52) U.S. Cl.
CPC ............. *A61K 31/451* (2013.01); *A61K 31/519* (2013.01); *A61K 31/55* (2013.01); *A61K 45/06* (2013.01)

(58) Field of Classification Search
None
See application file for complete search history.

(56) References Cited

U.S. PATENT DOCUMENTS

| 6,159,963 A | 12/2000 | Beasley et al. |
| 6,348,455 B1 | 2/2002 | Yelle |
| 2006/0058293 A1 | 3/2006 | Weber et al. |
| 2006/0189599 A1 | 8/2006 | Green et al. |
| 2006/0276412 A1 | 12/2006 | Tollefson |
| 2006/0287299 A1 | 12/2006 | Sheldon |

FOREIGN PATENT DOCUMENTS

| JP | 2006-071612 | 3/2006 |
| WO | WO 00/30648 | 6/2000 |
| WO | WO 00/30650 | 6/2000 |
| WO | WO 03/068207 | 8/2003 |
| WO | WO 2004/034996 | * 4/2004 |

OTHER PUBLICATIONS

Murphy et al (Alcohol 2:349-352, 1985).*
McBride et al (Pharmacol Biochem Behav 30:1045-1050, 1988).*
Simpson (J Family Practice 5(11), 2006).*
Withers et al., "Cocaine Abuse and Dependence," Journal of Clinical Psychopharmacology, vol. 15(1), pp. 63-78 (1995).
Albanese, "Decreased Substance Use in Chronically Psychotic Patients Treated with Clozapine," Am J Psychiatry, 151:5 (1994).
Albanese, "Safety and Efficacy of Risperidone in Substance Abusers with Psychosis," The American Journal on Addictions, 10:190-191 (2001).
Ashby et al., "Pharmacological Actions of the Atypical Antipsychotic Drug Clozapine: A Review," Synapse, 24:349-394 (1996).
Beresford et al., "Aripiprazole in Schizophrenia With Cocaine Dependence—A Pilot Study," Journal of Clinical Psychopharmacology, 25(4):363-366 (2005).
Bowers et al., "Psychotogenic Drug Use and Neuroleptic Response," Schizophrenia Bulletin, 16(1):81-85 (1990).
Brown et al., "A Randomized, Double-Blind, Placebo-Controlled Add-on Trial of Quetiapine in Outpatients With Bipolar Disorder and Alcohol Use Disorders," J Clin Psychiatry, 69(5):701-705 (2008).
Brown et al., "Cocaine and Amphetamine Use in Patients With Psychiatric Illness—A Randomized Trial of Typical Antipsychotic Continuation or Discontinuation," Journal of Clinical Psychopharmacology, 23(4):384-388 (2003).
Brown et al., "Quetiapine in bipolar disorder and cocaine dependence," Bipolar Disorders, 4:406-411 (2002).
Brown et al., "Switching Outpatients With Bipolar or Schizoaffective Disorders and Substance Abuse From Their Current Antipsychotic to Aripiprazole," J Clin Psychiatry, 66(6):756-760 (2005).
Brunette et al., "Clozapine Use and Relapses of Substance Use Disorder Among Patients With Co-occurring Schizophrenia and Substance Use Disorders," Schizophrenia Bulletin, 32(4):637-643 (2006).
Buckley, "New Antipsychotic Agents: Emerging Clinical Profiles," J Clin Psychiatry, 60(suppl. I):12-17 (1999).
Buckley et al., "Substance Abuse Among Patients With Treatment-Resistant Schizophrenia: Characteristics and Implications for Clozapine Therapy," Am J Psychiatry, 151(3):385-389 (1994).
Conley et al., "Olanzapine response in treatment-refractory schizophrenic patients with a history of substance abuse," Schizophrenia Research, 33:95-101(1998).
Drake et al., "The Effects of Clozapine on Alcohol and Drug Use Disorders Among Patients With Schizophrenia," Schizophrenia Bulletin, 26(2):441-449 (2000).
Green et al., "Alcohol and cannabis use in schizophrenia: effects of clozapine vs. risperidone," Schizophrenia Research, 60:81-85 (2003).
Green et al., "Clozapine for Comorbid Substance Use Disorder and Schizophrenia: Do Patients with Schizophrenia Have a Reward-Deficiency Syndrome That Can Be Ameliorated by Clozapine?", Harvard Rev Psychiatry, 6:287-296 (1999).
Green et al., "Clozapine reduces alcohol drinking in Syrian golden hamsters," Psychiatry Research, 128:9-20 (2004).
Green et al., "Clozapine Response and Plasma Catecholamines and Their Metabolites," Psychiatry Research, 46:139-149 (1992).
Green et al., "Haloperidol response and plasma catecholamines and their metabolites," Schizophrenia Research, 10:33-37 (1993).
Green et al., "Substance abuse and schizophrenia: Pharmacotherapeutic intervention," Journal of Substance Abuse Treatment, pp. 1-11 (2007).
Kalkman et al., "$\alpha_{2C}$-Adrenoceptor blockade by clozapine and other antipsychotic drugs," European Journal of Pharmacology, 462:33-40 (2003).

(Continued)

*Primary Examiner* — Craig Ricci
(74) *Attorney, Agent, or Firm* — Fish & Richardson P.C.

(57) ABSTRACT

Methods of treating and or preventing substance abuse/dependence, and alcohol abuse/dependence in particular. Combinations of medications are also disclosed.

6 Claims, 11 Drawing Sheets

(56) References Cited

OTHER PUBLICATIONS

Kapur et al., "Antipsychotic agents differ in how fast they come off the dopamine $D_2$ receptors. Implications for atypical antipsychotic action," Journal of Psychiatry & Neuroscience, 25(2):161-166 (2000).

Kapur et al., "Clinical and Theoretical Implications of 5-$HT_2$ and $D_2$ Receptor Occupancy of Clozapine, Risperidone, and Olanzapine in Schizophrenia," Am J Psychiatry, 156(2):286-293 (1999).

Keung et al., "Daidzin and daidzein suppress free-choice ethanol intake by Syrian Golden hamsters," Proc. Natl. Acad. Sci. USA, 90:10008-10012 (1993).

Lee et al., "Clozapine and substance abuse in patients with schizophrenia," Canadian journal of psychiatry, 43(8):855-6 (1998).

Littrell et al., "Olanzapine treatment for patients with schizophrenia and substance abuse," Journal of Substance Abuse Treatment, 21:217-221 (2001).

Longo, "Olanzapine for Cocaine Craving and Relapse Prevention in 2 Patients," J Clin Psychiatry, 63(7):595-596 (2002).

Longoria et al., "Quetiapine for Alcohol Use and Craving in Bipolar Disorder," Journal of Clinical Psychopharmacology, 24(1):101-101 (2004).

Marcus et al., "Reduction of comorbid substance abuse with clozapine," American Journal of Psychiatry, 152(6):959.

Martinez-Cano et al., "Methylphenidate in Stimulants Abuse: Three Case Reports," The American Journal on Addictions, 10:192-193 (2001).

McBride et al., "Animal Models of Alcoholism: Neurobiology of High Alcohol-Drinking Behavior in Rodents," Critical Reviews in Neurobiology, 12(4):339-369 (1998).

McEvoy et al., "Haloperidol increases smoking in patients with schizophrenia," Psychopharmacology, 119:124-126 (1995).

Noordsy, "Six-Month Outcomes for Patients Who Switched to Olanzpine Treatment," Psychiatric Services, 52(4):501-507 (2001).

Petrakis et al., "Atypical Antipsychotic Medication and Substance Use-Related Outcomes in the Treatment of Schizophrenia," The American Journal on Addictions, 15:44-49 (2006).

Potvin, "Quetiapine in patients with comorbid schizophrenia-spectrum and substance use disorders: an open-label trial," Current Medical Research and Opinion, 22(7):1277-1285 (2006).

Regier et al., "Comorbidity of Mental Disorders With Alcohol and Other Drug Abuse," JAMA, 264(19):2511-2518 (1990).

Sayers et al., "Cocaine Abuse in Schizophrenic Patients Treated With Olanzapine Versus Haloperidol," The Journal of Nervous and Mental Disease, 193(6):379-386 (2005).

Smelson et al., "The Efficacy of Olanzapine for Decreasing Cue-Elicited Craving in Individuals With Schizophrenia and Cocaine Dependence," Journal of Clinical Psychopharmacology, 26(1):9.

Smelson et al., "Risperidone Decreases Craving and Relapses in Individuals with Schizophrenia and Cocaine Dependence," Can J Psychiatry, 47(7):669-673 (2002).

Svensson, "α-Adrenoceptor modulation hypothesis of antipsychotic atypicality," Progress in Neuro-Psychopharmacology & Biological Psychiatry, 27:1145-1158 (2003).

Tsuang et al., "Olanzapine Treatment for Patients With Schizophrenia and Cocaine Abuse," J Clin Psychiatry, 63(12):1180-1181.

Wiesel et al., Central $D_1$- and $D_2$-Receptor Occupancy During Antipsychotic Drug Treatment, >> Prog. Neuro-Psychopharmacol. & Biol. Psychiat., 14:759-767 (1990).

Yoshimura et al., "Inhibitory effects of clozapine and other antipsychotic drugs on noradrenaline transporter in cultured bovine adrenal medullary cells," Psychopharmacology, 149:17-23 (2000).

Yovell et al., "Clozapine Reverses Cocaine Craving in a Treatment-Resistant Mentally Ill Chemical Abuser: A Case Report and a Hypothesis," Journal of Nervous and Mental Disease, 182(10):591-592 (1994).

Zimmet et al., "Effects of Clozapine on Substance Use in Patients With Schizophrenia and Schizoaffective Disorder: A Retrospective Survey," J Clin Psychopharmacol, 20(1):94-94 (2000).

Ziedonis et al., "Adjunctive Desipramine in the Treatment of Cocaine Abusing Schizophrenics," Psychopharmacology Bulletin, vol. 28, No. 3 (1992).

Examination Report for EP 08826643.2 mailed Apr. 21, 2011.

Notice of Reasons for Rejection; Mar. 27, 2013; PCT/US2008/052811;8 pp.

Extended European Search Report from corresponding European Application No. 12156587.3 dated Mar. 20, 2012.

\* cited by examiner

FIGURE 1: PRIOR ART

Green et al, Psychiatry Research, 2004

CLOZAPINE & HALOPERIDOL on Initiation of Alcohol Drinking in P-RATS

\* p < .05, vs VEH
\*\* p < .001, vs VEH
‡ p < .001, vs 1 mg/kg HAL

FIGURE 4

CLOZAPINE & HALOPERIDOL on Initiation of Alcohol Drinking in P-RATS

\* $p < .001$, vs VEH
‡ $p < .001$, vs. HAL

FIGURE 11

COMBINATIONS OF DOPAMINE D2 RECEPTOR BLOCKADE WITH NOREPINEPHRINE REUPTAKE INHIBITION AND WITH NOREPINEPHRINE ALPHA 2 RECEPTOR BLOCKADE

RELATED CASES

I claim priority from my earlier-filed applications U.S. Ser. No. 61/007,117 filed Dec. 11, 2007 and U.S. Ser. No. 60/887,657 filed Feb. 1, 2007, each of which is hereby incorporated by reference in its entirety.

REFERENCE TO FEDERALLY SPONSORED RESEARCH OR DEVELOPMENT

This invention was funded at least in part by NIH grant R03AA014644. The government has certain rights in this invention.

TECHNICAL FIELD this invention relates to treating alcohol and/or other substance abuse or dependence, and to compositions used for such treatment.

BACKGROUND

Substance use disorder (i.e., substance abuse or substance dependence) occurs commonly in patients with schizophrenia and worsens its clinical course. Commonly abused substances include alcohol, cannabis and cocaine, and such abuse occurs at a rate of greater than 3 times the rate seen in the general population. Moreover, tobacco smoking occurs in over 75% of the patients with schizophrenia. The standard or typical antipsychotic medications commonly used to treat schizophrenia do not appear to be helpful in lessening the use of substances in this population. Data from our group and others, however, suggest that the atypical antipsychotic clozapine appears to limit alcohol, cannabis and cocaine abuse in this population, but its toxicity limits widespread use[1].

[1] Green, A. I., et al., Clozapine for comorbid substance use disorder and schizophrenia: do patients with schizophrenia have a reward-deficiency syndrome that can be ameliorated by clozapine? Harv Rev Psychiatry, 1999. 6(6): p. 287-96; Green, A. I., et al., Substance abuse and schizophrenia: Pharmacotherapeutic intervention. J Subst Abuse Treat, 2008. 34(1): p. 61-71; Brunette, M. F., et al., Clozapine use and relapses of substance use disorder among patients with co-occurring schizophrenia and substance use disorders. Schizophr Bull, 2006. 32(4): p. 637-43. Drake, R. E., et al., The effects of clozapine on alcohol and drug use disorders among patients with schizophrenia. Schizophr Bull, 2000. 26(2): p. 441-9; Green, A. I., et al., Alcohol and cannabis use in schizophrenia: effects of clozapine vs. risperidone. Schizophr Res, 2003. 60(1): p. 81-5; Zimmet, S. V., et al., Effects of clozapine on substance use in patients with schizophrenia and schizoaffective disorder: a retrospective survey. J Clin Psychopharmacol, 2000. 20(1): p. 94-8; US 2006-0189599.

SUMMARY

We have discovered, based on a series of experiments in animals, that medications exhibiting a combination of dopamine D2 receptor blockade (typically a weak blockade) with norepinephrine reuptake inhibition (i.e., inhibition of the norepinephrine transporter) are useful treatments for patients with, or at risk for, alcohol and/or other substance abuse/dependence (including those patients who have both alcohol and/or other substance abuse/dependence with a co-occurring psychiatric disorder such as schizophrenia or bipolar disorder). The presence of a norepinephrine alpha 2 receptor blockade (also a property of clozapine) in such a medication (in combination with the other effects, i.e., dopamine D2 receptor blockade and norepinephrine reuptake inhibition) may also be helpful in limiting alcohol (or other substance) abuse in such individuals. Substances of abuse in this context include not only alcohol but also opioids, including heroin and oxyContin®, cannabis, cocaine, amphetamines, tobacco and others.

Another aspect of the invention features combinations of medications exhibiting the above-described activities. The combinations include: a) for the dopamine D2 receptor antagonist activity, risperidone, paliperidone, haloperidol, olanzapine, quetiapine, ziprasidone, aripiprazole, fluphenazine or other drugs with D2 receptor blockade (antagonistic) properties; b) for norepinephrine reuptake blockade (inhibition), desipramine or reboxetine, or other drugs with norepinephrine reuptake inhibition properties; c) for alpha 2 antagonist activity, idazoxan and yohimbine, or other drugs with norepinephrine alpha 2 receptor antagonistic effects.

Compositions having combinations of medications, as well as methods of therapy using combinations of medications, are featured, in which the multiple activities of the medication are provided by more than one specific medicinal compound.

Accordingly, the invention generally features methods of treating and or preventing substance abuse/dependence, and alcohol abuse/dependence in particular. The medications used in the invention are described above. The patients to be treated according to the invention are those with a history or a risk of alcohol or substance abuse/dependence.

The compounds to be administered can be formulated into a suitable pharmaceutical preparation by known techniques, for example well known tablet and capsule formulations. Such formulations typically comprise the active agent (or the agent in a salt form) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include oral, intravenous, intradermal, subcutaneous, transdermal (topical), transmucosal (e.g. intranasal), and rectal.

By far the most convenient route of administration is oral (ingestion). Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

DETAILED DESCRIPTION

The details of one or more embodiments of the invention are set forth in the accompanying drawings and the description below. Other features, objects, and advantages of the invention will be apparent from the description and drawings, and from the claims.

The following Examples provide a detailed description of the invention.

General Methods

The animal models that we have used in our experiments include the Syrian golden hamster (Mesocricetus auratus, Harlan Inc.) and the alcohol preferring P rat (Indiana University). Both animals prefer an alcohol solution over water when given a choice between the two fluids and they consume large quantities of alcohol on a daily basis. However, while the hamster is an out-bred rodent, which has a natural preference for alcohol, the P rat has been bred over multiple generations through the selective mating of rats with high alcohol preference. Both the hamster and the P rat have been used by alcohol researchers to screen medications for treatment of alcoholism. Keung, W. M. and B. L. Vallee, Daidzin and daidzein suppress free-choice ethanol intake by Syrian golden hamsters. Proc Natl Acad Sci USA, 1993. 90(21): p. 10008-12; McBride, W. J. and T. K. Li, Animal models of alcoholism: neurobiology of high alcohol-drinking behavior in rodents. Crit Rev Neurobiol, 1998. 12(4): p. 339-69.

Two types of studies were conducted in hamsters and P rats. The first type of study assessed the ability of drugs (or drug combinations) to decrease chronic alcohol drinking in these animals. In these studies, drug treatment began after the animals had been drinking alcohol for several weeks. The second type of study assessed the effects of drugs (or drug combinations) on the ability of the animals to initiate alcohol drinking. The animals in the latter type of study received drug treatment several days prior to and during the initial weeks of exposure to alcohol. All animals were given 24 hours/day access to 10-15% alcohol and water in two separate drinking bottles. Groups of animals (n=6-10/group) received daily injections of the specific drug or drug combination or vehicle for up to 4 weeks.

Examples 1 (Prior Art) and 2

Figure 1:
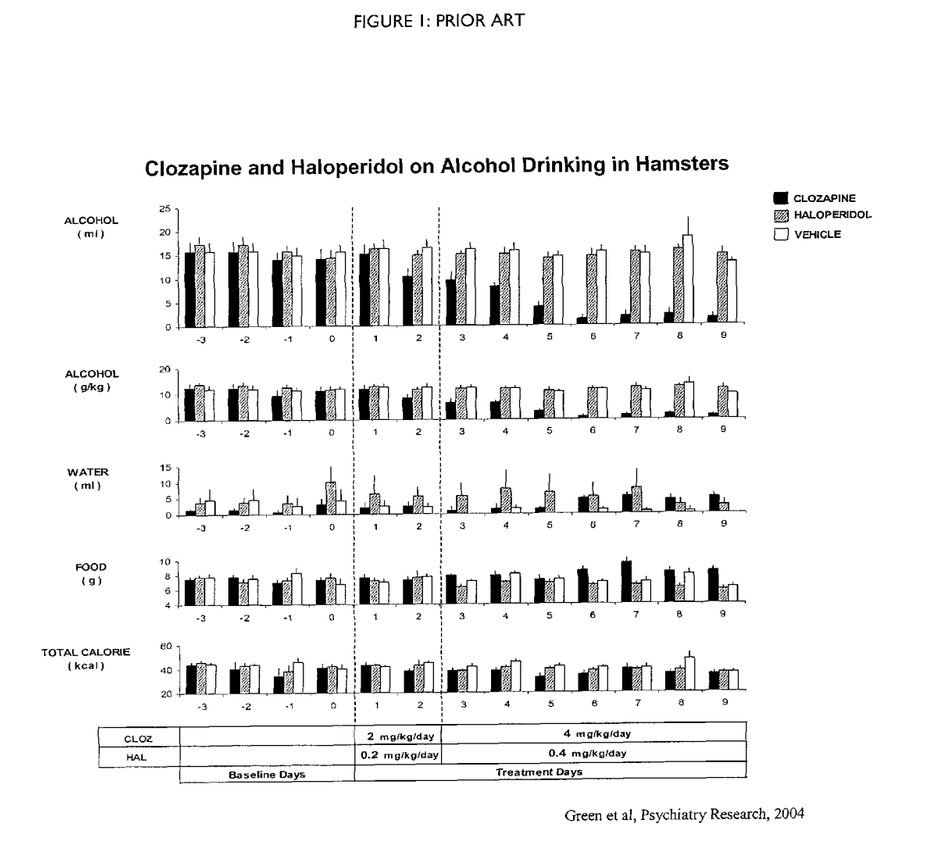
FIG. 1 (PRIOR ART) is a graph depicting the results of the experiment reported in Example 1: Clozapine and Halperidol on Alcohol Drinking in Hamsters, taken from Green, A. I., et al., Clozapine reduces alcohol drinking in Syrian golden hamsters. Psychiatry Res, 2004. 128(1): p. 9-20.
Figure 2:
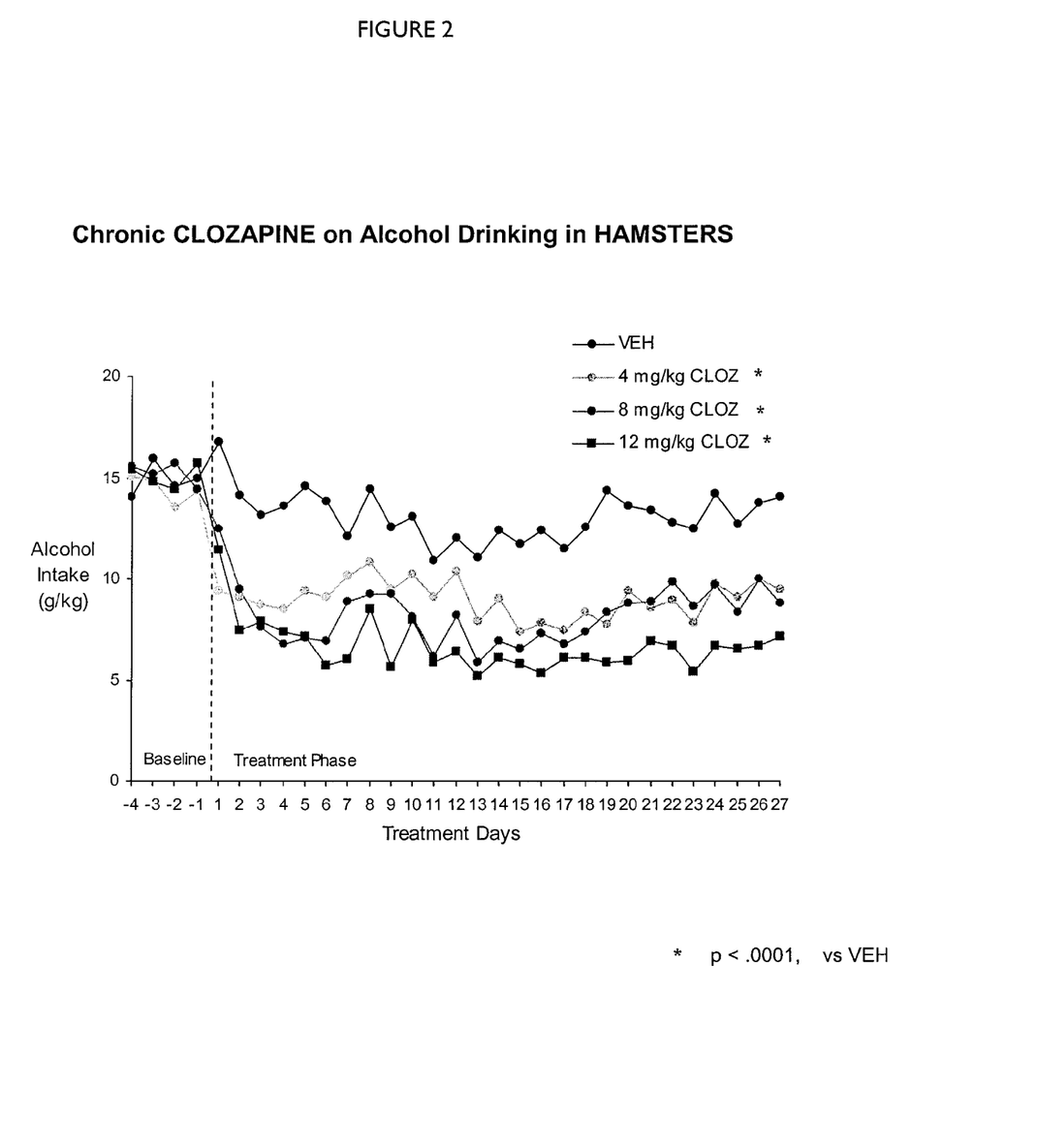
FIG. 2 is a graph depicting the results of the experiment reported in Example 2: Chronic Clozapine on Alcohol Drinking in Hamsters.

In one study, we demonstrated that clozapine (CLOZ), but not the typical antipsychotic drug haloperidol (HAL), dramatically decreased chronic alcohol drinking in the Syrian golden hamster more than vehicle (VEH) (FIG. 1). Green, A. I., et al., Clozapine reduces alcohol drinking in Syrian golden hamsters. Psychiatry Res, 2004. 128(1): p. 9-20. No dose of haloperidol tested had an effect on alcohol drinking in the hamster. Moreover, in another study with unpublished data, as seen in FIG. 2, we demonstrated that this effect of clozapine is chronic, lasting at least 1 month.

Examples 3 and 4

Figure 3:
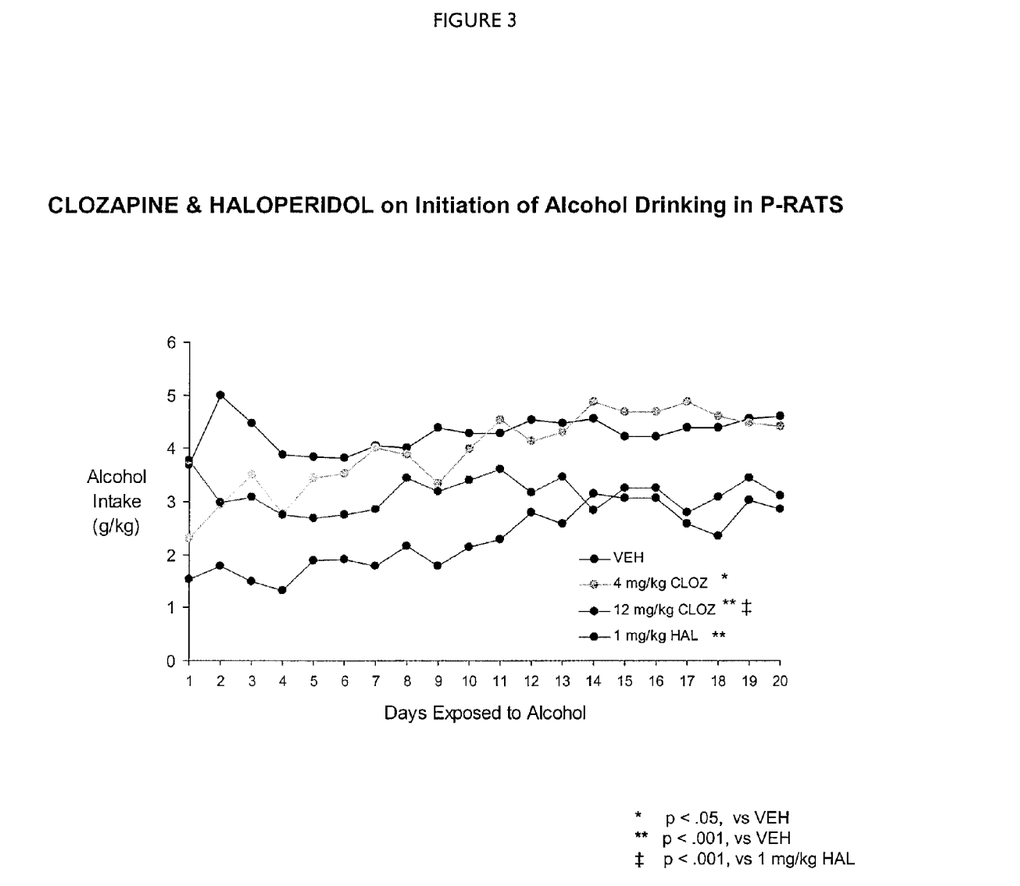
FIG. 3 is a graph depicting the results of the experiment reported in Example 3: Clozapine and Haloperidol on Initiation of Alcohol Drinking in P-rats.
Figure 4:
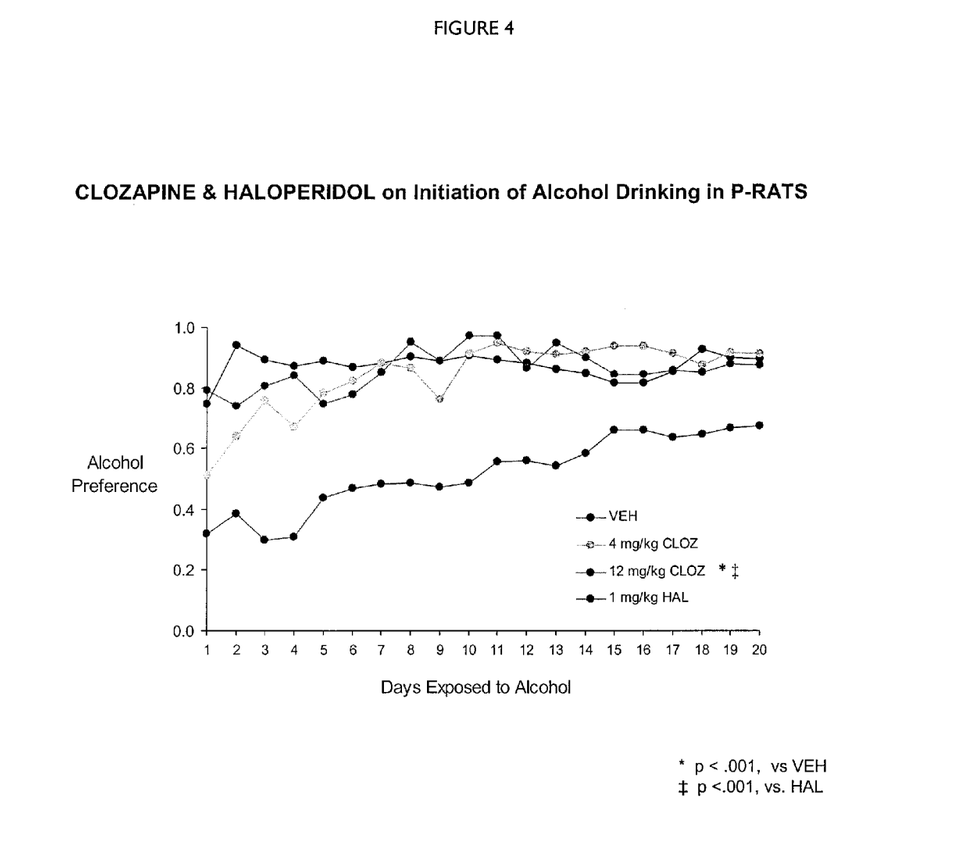
FIG. 4 is a graph depicting the results of the experiment reported in Example 4: Clozapine and Haloperidol on Initiation of Alcohol Drinking in P-Rats.

In another study, we demonstrated that clozapine (CLOZ) also decreases the initiation of alcohol drinking in the alcohol-preferring P rat, as compared to vehicle (VEH) and haloperidol (HAL) (FIG. 3). This can be seen most dramatically by looking at alcohol preference (the % of liquid consumed that comes from the alcohol bottle)—FIG. 4. Clozapine dramatically decreases alcohol preference during the initiation of alcohol drinking.

Example 5

Figure 5:
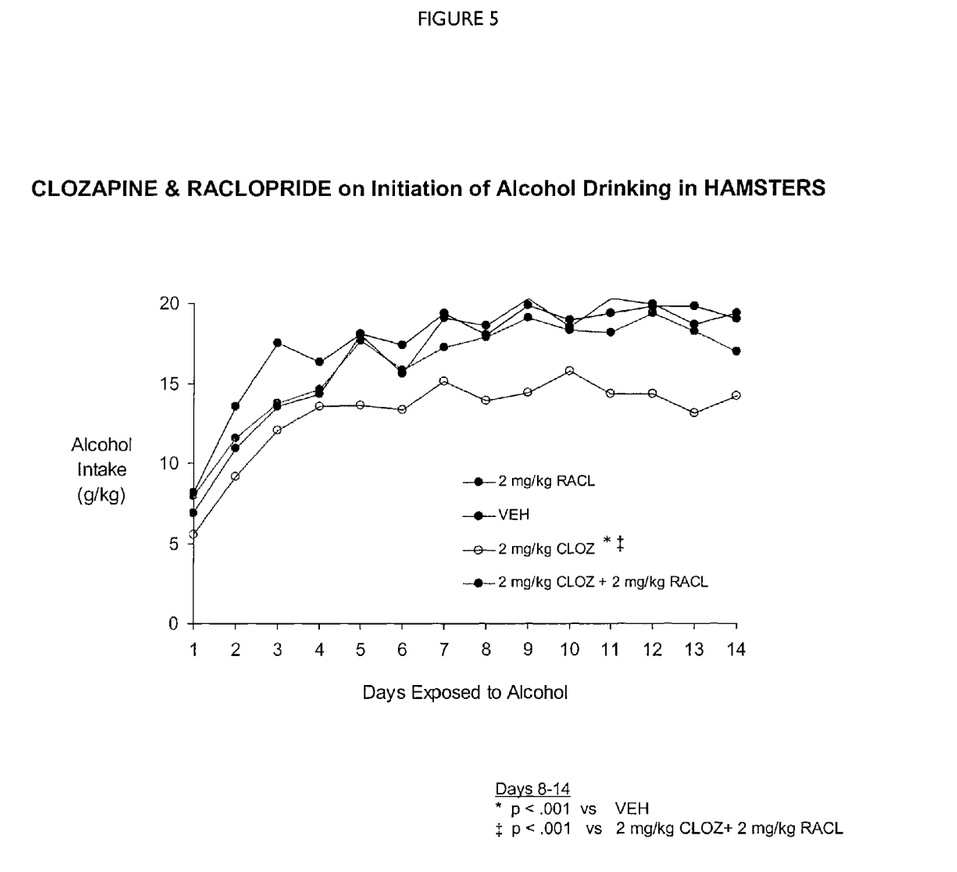
FIG. 5 is a graph depicting the results of the experiment reported in Example 5: Clozapine and Raclopride on Initiation of Alcohol Drinking in Hamsters.

In Example 5 (FIG. 5), we have demonstrated that clozapine (in this case a low dose) also blunts the initiation of alcohol drinking in the hamster. We have also demonstrated in FIG. 5 that by adding raclopride (RACL, a potent D2/D3 receptor antagonist) to a low dose of clozapine, this effect of clozapine on the initiation of alcohol drinking by the hamster is lost. This finding is consistent with our proposition that clozapine's effect on alcohol drinking is at least partially related to its weak D2 receptor blocking ability.

Example 6

Figure 6:
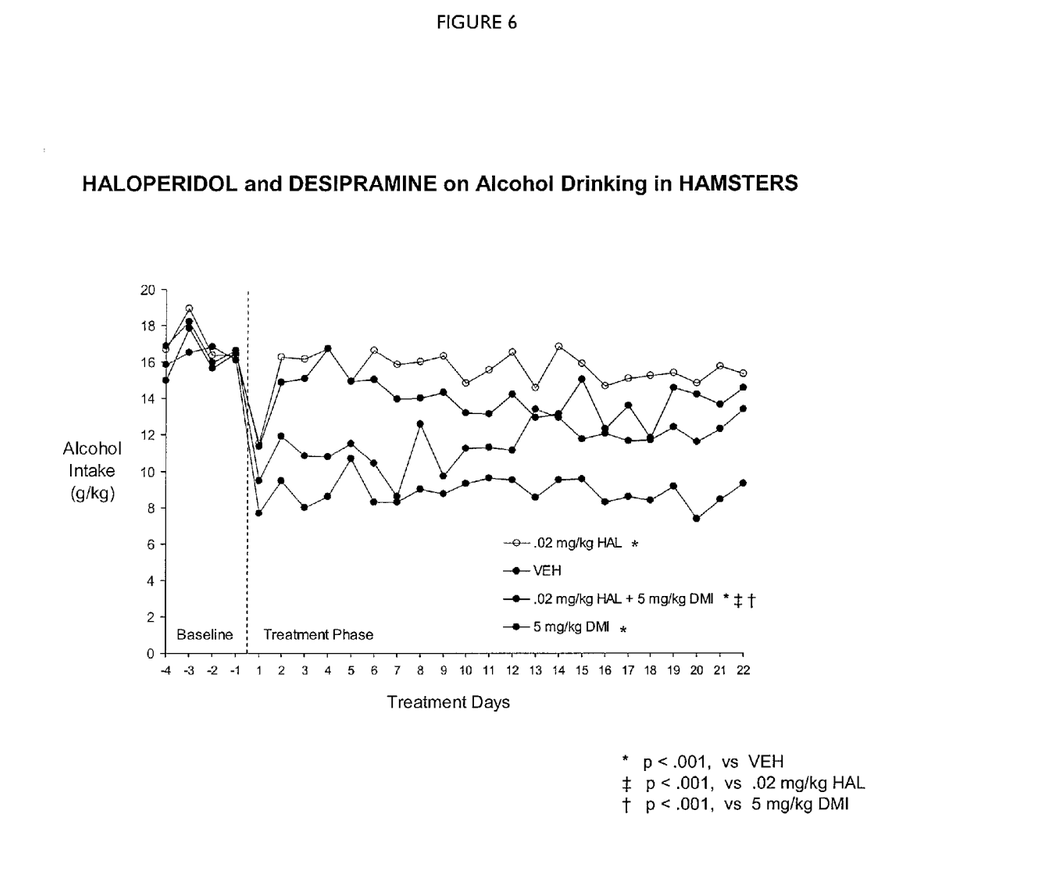
FIG. 6 is a graph depicting the results of the experiment reported in Example 6: Haloperidol and Desipramine on Alcohol Drinking Hamsters.

In the hamster, as noted above, haloperidol has very little effect on chronic alcohol drinking. However, if the norepinephrine reuptake inhibitor desipramine (DMI) is added to low dose haloperidol (HAL), it decreases the alcohol drinking more than does desipramine alone (FIG. 6). This supports our proposition that a weak dopamine D2 receptor blocker plus a norephinephrine reuptake inhibitor decreases alcohol drinking.

Examples 7 and 8

Figure 7:
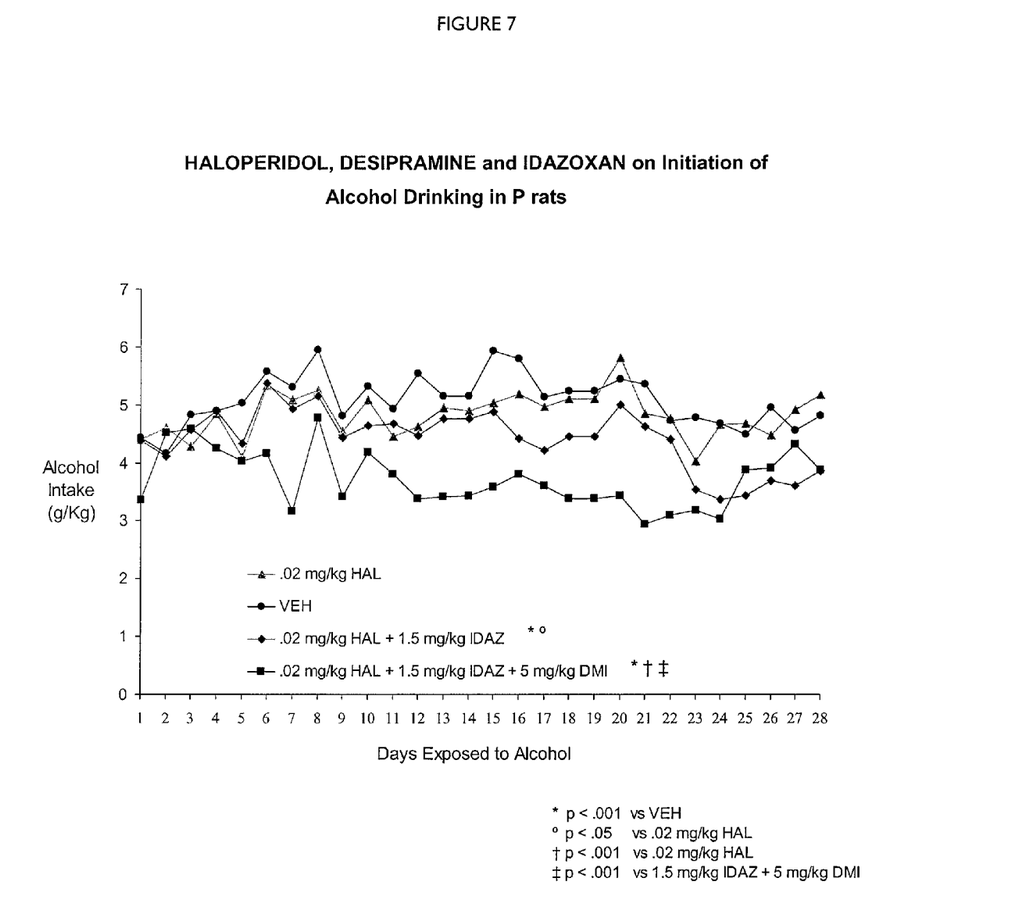
FIG. 7 is a graph depicting the results of the experiment reported in Example 7: Haloperidol, Desipramine and Idazoxan on Initiation of Alcohol Drinking in P-Rats.
Figure 8:
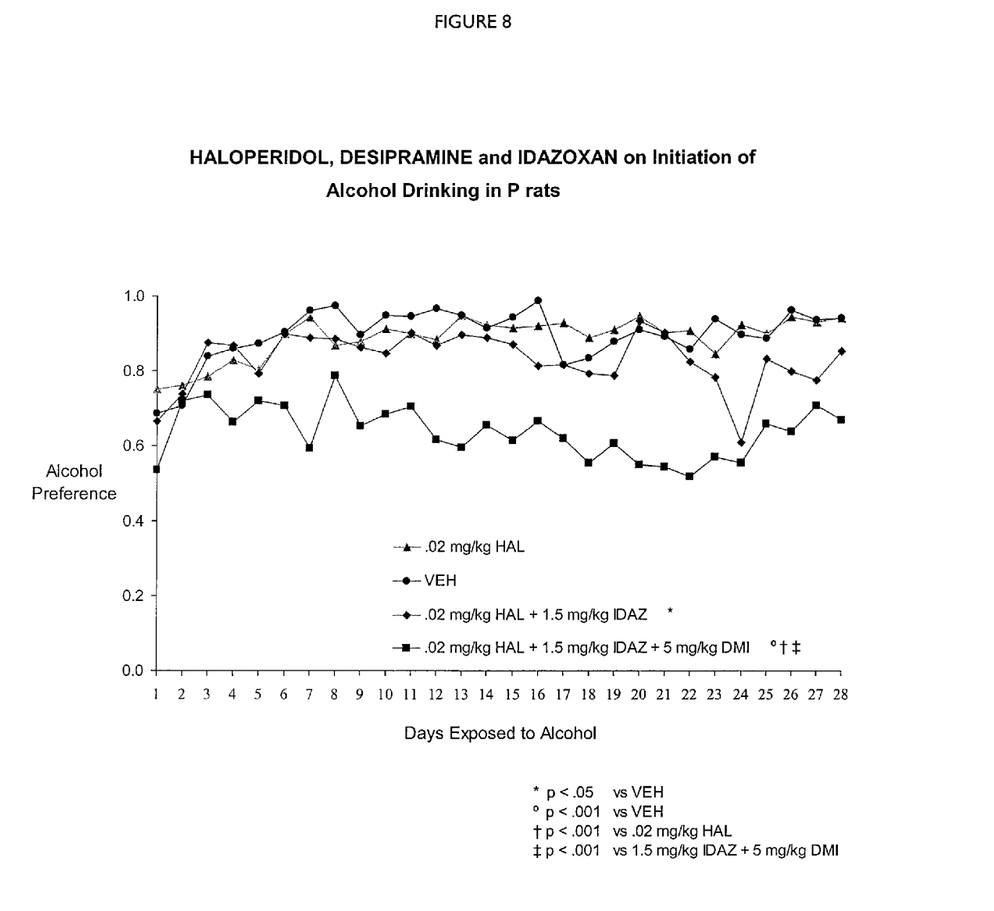
FIG. 8 is a graph depicting the results of the experiment reported in Example 8: Haloperidol, Desipramine and Idazoxan on Initiation of Alcohol Drinking in P rats.

Low dose haloperidol has minimal ability to blunt the initiation of alcohol drinking by the P rat. However, adding the alpha 2 receptor blocker idazoxan (IDAZ) to low-dose haloperidol modestly increases the ability of haloperidol to blunt the initiation of alcohol drinking. However, if the norepinephrine reuptake inhibitor desipramine (DMI) is added these two drugs, it dramatically increases the ability of them to decrease alcohol drinking and alcohol preference (FIGS. 7 and 8). This effect is consistent with our proposition that a weak dopamine D2 receptor blocking effect coupled with a potent norepinephrine alpha 2 receptor blocker and a norepinephrine reuptake inhibitor will decrease alcohol drinking.

Examples 9-11

Figure 9:
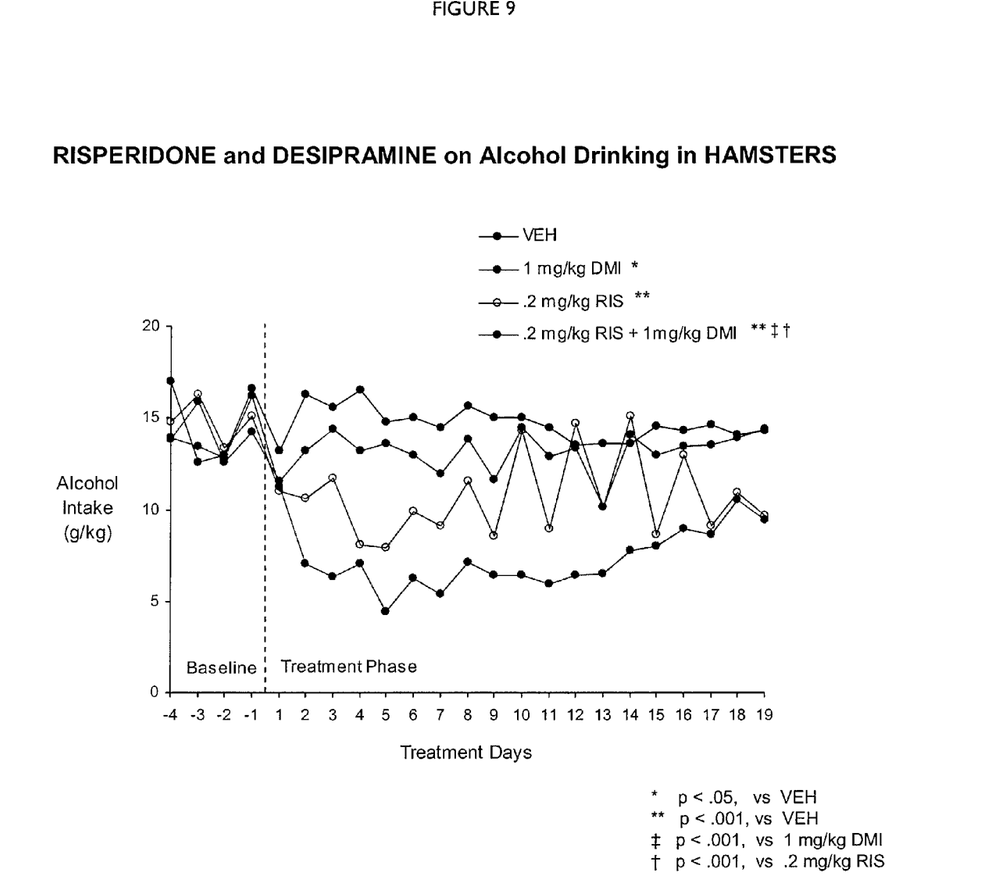
FIG. 9 is a graph depicting the results of the experiment reported in Example 9: Risperidone and Desipramine on Alcohol Drinking in Hamsters.
Figure 10:
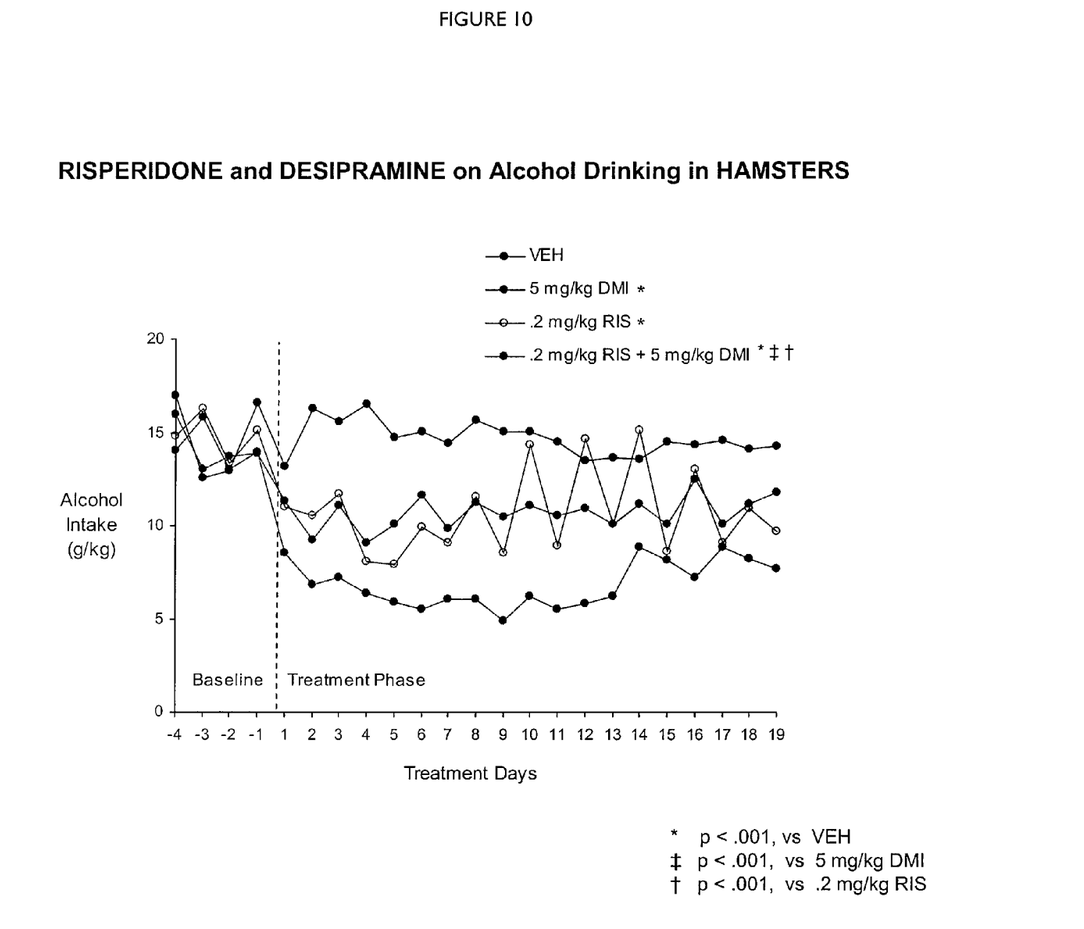
FIG. 10 is a graph depicting the results of the experiment reported in Example 10: Risperidone and Desipramine on Alcohol Drinking in Hamsters.
Figure 11:
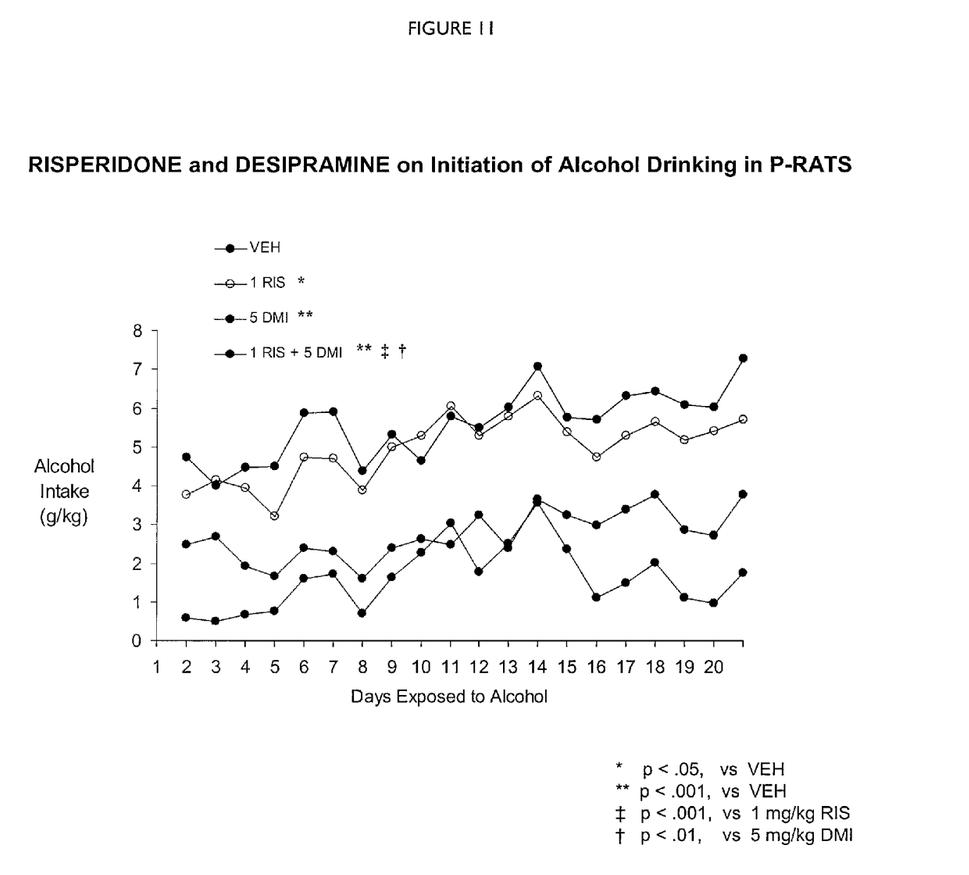
FIG. 11 is a graph depicting the results of the experiment reported in Example 11: Risperidone and Desipramine on Initiation of Alcohol Drinking in P-rats.

Lastly, we have demonstrated that a low dose of risperidone (RISP), a drug with a potent dopamine D2 receptor blocking ability, has only a modest effect on alcohol drinking in both the hamster (on chronic drinking) and the P rat (on the initiation of alcohol drinking). We have further shown that the addition of the norepinephrine reuptake inhibitor desipramine (DMI) to risperidone causes risperidone to limit alcohol drinking. Moreover, this effect, which we have seen in both the hamster and the P rat, is more dramatic than with desipramine alone (FIGS. 9, 10, and 11). This effect is consistent with our proposition that a weak D2 receptor blocker (weak because of the low dose of risperidone) coupled with a norepinephrine reuptake inhibitor will decrease alcohol drinking. Moreover, since risperidone is also a blocker of the norepinephrine alpha 2 receptor (as well as the D2 receptor), its blockade of the alpha 2 receptor (in combination with its D2 receptor blockade) may contribute to allowing the norephinephrine reuptake inhibitor desipramine to convert risperidone into a drug that decreases alcohol drinking.

We conclude that the combination of a weak dopamine dopamine D2 receptor blocker (antagonist) and a potent norepinephrine reuptake inhibitor may produce a drug that shares with clozapine the ability to limit alcohol drinking. We further conclude that addition of a norepinephrine alpha 2 receptor blocker (antagonist) may contribute to the ability of a composition with these characteristics to limit alcohol drinking. Our findings suggest medications containing these properties as a therapeutic agent in patients with schizophrenia and alcohol or substance abuse/dependence. Since the medications that we have tested limit alcohol drinking in animal models of alcoholism, and since, moreover, patients with alcohol use disorder and substance use disorder may share some biologic characteristics (i.e., disordered brain reward circuitry) of patients with schizophrenia, we conclude that a medication with these characteristics should be effective as well in patients with alcohol use disorder and/or substance use disorder who do not have schizophrenia.

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating alcohol abuse or dependence in a patient suffering from alcohol abuse or dependence, comprising administering to a patient in need thereof a combination comprising desipramine and at least a second compound selected from the group consisting of risperidone, paliperidone and haloperidol, in an amount effective to limit alcohol intake.

2. The method of claim 1 in which the second compound is risperidone.

3. The method of claim 1 in which the second compound is haloperidol.

4. The method of claim 1 or claim 2 in which the composition further comprises a norepinephrine alpha 2 receptor antagonist.

5. The method of claim 4 in which the norepinephrine alpha 2 receptor antagonist is idazoxan, yohimbine, atipamezole, mirtazapine, mianserin, phenoxybenzamine, buspirone, or mianserin.

6. A method for treating alcohol abuse or dependence in a patient suffering from alcohol abuse or dependence, comprising administering to a patient in need thereof a combination comprising desipramine and iloperidone, in an amount effective to limit alcohol intake.

* * * * *